(12) United States Patent
Ellingson

(10) Patent No.: US 9,675,806 B2
(45) Date of Patent: Jun. 13, 2017

(54) CARDIAC PACING DURING MEDICAL PROCEDURES

(71) Applicant: Medtronic, Inc., Minneapolis, MN (US)

(72) Inventor: Michael L. Ellingson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 729 days.

(21) Appl. No.: 13/647,705

(22) Filed: Oct. 9, 2012

(65) Prior Publication Data

US 2014/0100624 A1   Apr. 10, 2014

(51) Int. Cl.
*A61N 1/368* (2006.01)

(52) U.S. Cl.
CPC .................................. *A61N 1/3688* (2013.01)

(58) Field of Classification Search
CPC .................................................. A61N 1/3688
USPC ............. 607/2, 5, 9, 11, 14, 27, 30; 600/411
See application file for complete search history.

(56) References Cited

U.S. PATENT DOCUMENTS

| | | |
|---|---|---|
| 3,949,759 A | 4/1976 | Brownlee et al. |
| 4,091,818 A | 5/1978 | Brownlee et al. |
| 4,344,437 A | 8/1982 | Markowitz |
| 4,572,192 A | 2/1986 | Jackman et al. |
| 4,878,497 A | 11/1989 | Callaghan et al. |
| 5,076,272 A | 12/1991 | Ferek-Petric |
| 5,374,280 A | 12/1994 | den Dulk |
| 5,431,692 A | 7/1995 | Hansen et al. |
| 5,480,414 A | 1/1996 | Stroebel et al. |
| 5,607,458 A | 3/1997 | Causey, III et al. |
| 5,643,326 A | 7/1997 | Weiner et al. |
| 5,817,136 A | 10/1998 | Nappholz et al. |
| 5,846,264 A | 12/1998 | Andersson et al. |
| 5,928,271 A | 7/1999 | Hess et al. |

(Continued)

FOREIGN PATENT DOCUMENTS

| | | |
|---|---|---|
| EP | 0031229 A2 | 7/1981 |
| WO | 2010/039877 A1 | 4/2010 |

OTHER PUBLICATIONS (PCT/US2013/061364) PCT Notification of Transmittal of the International Search Report and the Written Opinion of the International Searching Authority, Mailed Dec. 10, 2013, 9 pages.

*Primary Examiner* — Christopher A Flory

(57) ABSTRACT

An implantable medical device may comprise a therapy module configured to generate pacing therapy for a heart of a patient and a control module configured to control the therapy module. The control module may also be configured to detect a condition indicative of the presence of a magnetic resonance imaging (MRI) device and switch operation from a first pacing therapy program to a second pacing therapy program in response to detecting the condition indicative of the presence of the MRI device. While operating in the second pacing therapy program, control module may control the therapy module to generate a pacing pulse to an atrium of the heart of the patient during a time period between the end of an atrial refractory period of a previous atrial depolarization and the end of a ventricular refractory period of a previous ventricular depolarization corresponding to the previous atrial depolarization.

20 Claims, 5 Drawing Sheets

(56) References Cited

U.S. PATENT DOCUMENTS

| | | | |
|---|---|---|---|
| 6,061,594 A | 5/2000 | Zhu et al. | |
| 6,188,926 B1 | 2/2001 | Vock | |
| 6,856,835 B2 | 2/2005 | Bardy et al. | |
| 6,895,272 B2 | 5/2005 | Seim et al. | |
| 7,031,773 B1 | 4/2006 | Levine et al. | |
| 7,146,212 B2 | 12/2006 | Bardy et al. | |
| 7,212,855 B1 | 5/2007 | Kroll et al. | |
| 7,225,020 B1 | 5/2007 | Kroll et al. | |
| 7,260,432 B2 | 8/2007 | Kramer et al. | |
| 7,363,081 B1 | 4/2008 | Kroll et al. | |
| 7,369,898 B1* | 5/2008 | Kroll et al. | 607/63 |
| 7,424,323 B1 | 9/2008 | Reiss et al. | |
| 7,474,247 B1 | 1/2009 | Heinks et al. | |
| 7,561,915 B1 | 7/2009 | Cooke et al. | |
| 7,693,568 B2 | 4/2010 | Zeijlemaker | |
| 7,769,465 B2 | 8/2010 | Matos | |
| 7,860,563 B2* | 12/2010 | Foreman et al. | 607/2 |
| 8,200,334 B1* | 6/2012 | Min et al. | 607/27 |
| 2001/0034538 A1 | 10/2001 | Olson et al. | |
| 2003/0083712 A1 | 5/2003 | Rueter et al. | |
| 2003/0144698 A1 | 7/2003 | Ujhelyi et al. | |
| 2003/0144705 A1* | 7/2003 | Funke | 607/27 |
| 2004/0039422 A1 | 2/2004 | Russie et al. | |
| 2004/0102811 A1 | 5/2004 | Schwartz et al. | |
| 2004/0162593 A1 | 8/2004 | Jorgenson et al. | |
| 2004/0254614 A1 | 12/2004 | Spinelli et al. | |
| 2005/0038474 A1 | 2/2005 | Wool | |
| 2005/0137640 A1 | 6/2005 | Freeberg et al. | |
| 2006/0074454 A1 | 4/2006 | Freeberg | |
| 2006/0167496 A1 | 7/2006 | Nelson et al. | |
| 2006/0173493 A1 | 8/2006 | Armstrong et al. | |
| 2006/0247697 A1 | 11/2006 | Sharma et al. | |
| 2006/0293591 A1* | 12/2006 | Wahlstrand et al. | 600/423 |
| 2006/0293717 A1 | 12/2006 | Sathaye et al. | |
| 2007/0203523 A1 | 8/2007 | Betzold | |
| 2007/0265670 A1 | 11/2007 | Lang et al. | |
| 2007/0293898 A1 | 12/2007 | Sheldon et al. | |
| 2007/0293899 A1 | 12/2007 | Sheldon et al. | |
| 2008/0058880 A1 | 3/2008 | Kim et al. | |
| 2008/0071319 A1 | 3/2008 | Sathaye et al. | |
| 2008/0103536 A1 | 5/2008 | Xiao | |
| 2008/0103537 A1 | 5/2008 | Sigg et al. | |
| 2009/0149905 A1 | 6/2009 | Lyden et al. | |
| 2009/0157135 A1 | 6/2009 | Perschbacher et al. | |
| 2009/0299424 A1* | 12/2009 | Narayan | 607/9 |
| 2010/0010554 A1 | 1/2010 | Reiss | |
| 2010/0094370 A1 | 4/2010 | Levin et al. | |
| 2010/0114199 A1 | 5/2010 | Krause et al. | |
| 2010/0114224 A1 | 5/2010 | Krause et al. | |
| 2010/0137945 A1 | 6/2010 | Gadagkar et al. | |
| 2010/0191236 A1 | 7/2010 | Johnson et al. | |
| 2010/0198310 A1 | 8/2010 | Ellingson | |
| 2010/0211123 A1* | 8/2010 | Stubbs et al. | 607/4 |
| 2010/0292745 A1 | 11/2010 | Shuros et al. | |
| 2010/0298901 A1 | 11/2010 | Sommer et al. | |
| 2010/0318160 A1* | 12/2010 | Stevenson et al. | 607/63 |
| 2011/0093040 A1* | 4/2011 | Ellingson et al. | 607/59 |
| 2011/0093046 A1* | 4/2011 | Ellingson et al. | 607/60 |
| 2011/0106204 A1* | 5/2011 | Yoon et al. | 607/30 |
| 2011/0106212 A1* | 5/2011 | Ellingson et al. | 607/59 |
| 2011/0160791 A1* | 6/2011 | Ellingson et al. | 607/27 |
| 2011/0196447 A1* | 8/2011 | McClure et al. | 607/59 |
| 2011/0196450 A1* | 8/2011 | McClure et al. | 607/60 |
| 2012/0101544 A1* | 4/2012 | Hoberman et al. | 607/28 |
| 2012/0221068 A1* | 8/2012 | Ellingson | 607/17 |
| 2012/0226140 A1* | 9/2012 | Min et al. | 600/411 |
| 2012/0253425 A1 | 10/2012 | Yoon et al. | |
| 2012/0277815 A1* | 11/2012 | Stancer et al. | 607/14 |
| 2012/0277817 A1* | 11/2012 | Ellingson et al. | 607/25 |
| 2012/0277818 A1* | 11/2012 | Stancer et al. | 607/32 |

* cited by examiner

CARDIAC PACING DURING MEDICAL PROCEDURES

TECHNICAL FIELD

This disclosure relates generally to cardiac pacing during medical procedures.

BACKGROUND

A wide variety of implantable medical systems that deliver a therapy or monitor a physiologic condition of a patient have been clinically implanted or proposed for clinical implantation in patients. The implantable medical system may include an implantable medical lead connected to an implantable medical device (IMD). For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads.

Patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field may be generated by a primary magnet within the MRI device and may be present prior to initiation of the MRI procedure. The gradient magnetic fields may be generated by electromagnets of the MRI device and may be present during the MRI procedure. The RF fields may be generated by transmitting/receiving coils of the MRI device and may be present during the MRI procedure. If the patient undergoing the MRI procedure has an implantable medical system, the various fields produced by the MRI device may have an effect on the operation of the implantable medical system. As such, the IMD is typically configured into an MR conditional operating mode prior to the MRI scan to reduce, and possibly eliminate, the effect on the operation of the IMD.

SUMMARY

Current clinical practice is to select a pacing therapy program for use during the MR conditional mode that provides asynchronous pacing for pacemaker-dependent patients at a rate above the intrinsic rate of the patient and to limit the duration of the asynchronous pacing. However, there is a possibility that the condition of the patient could change during the period of time their pacemaker is programmed to an asynchronous pacing mode. For example, some patients may experience an increase in their intrinsic heart rate during asynchronous pacing (e.g., due to increased anxiety when in the bore of an MRI scanner), which could result in competitive pacing. The pacing techniques of this disclosure provide a mechanism to reduce the likelihood of competitive pacing by decreasing the intrinsic heart rate during pacing therapy programs that provide pacing independent of underlying cardiac activity. In addition, pacing at a rate closer to the intrinsic heart rate of the patient could reduce the likelihood of symptoms that are sometimes induced by asynchronous pacing at higher rates.

In accordance with the techniques of this disclosure, the pacing therapy program utilized during the MR conditional mode provides an atrial pacing pulse after the atrial refractory period of a previous atrial depolarization expires, but prior to expiration of the ventricular refractory period of a ventricular depolarization corresponding to the previous atrial depolarization. The result of the atrial pacing pulse after the atrial refractory period of the previous atrial depolarization and before the expiration of the ventricular refractory period is two atrial depolarizations during a single cardiac cycle. Such a technique may be utilized when the pacing therapy program of the MR conditional mode is a synchronous pacing therapy program or a therapy pacing program that provides pacing independent of the underlying cardiac activity.

In one example, this disclosure is directed to an implantable medical device that includes a therapy module configured to generate pacing therapy for a heart of a patient and a control module configured to detect a condition indicative of the presence of a magnetic resonance imaging (MRI) device, switch operation from a first pacing therapy program to a second pacing therapy program in response to detecting the condition indicative of the presence of the MRI device, and while operating in the second pacing therapy program, control the therapy module to generate a pacing pulse to an atrium of the heart of the patient during a time period between the end of an atrial refractory period of a previous atrial depolarization and the end of a ventricular refractory period of a previous ventricular depolarization corresponding to the previous atrial depolarization.

In another example, this disclosure is directed to a method that includes operating an implantable medical device (IMD) in a first pacing therapy program, detecting a condition indicative of the presence of a magnetic resonance imaging (MRI) device, switching operation of the IMD from the first pacing therapy program to a second pacing therapy program in response to detecting the condition indicative of the presence of the MRI device, and while operating in the second pacing therapy program, delivering a pacing pulse to an atrium of a heart of a patient during a time period between the end of an atrial refractory period of a previous atrial depolarization and the end of a ventricular refractory period of a previous ventricular depolarization corresponding to the previous atrial depolarization.

In a further example, this disclosure is directed to a computer-readable storage medium comprising instructions, that when executed, cause a processor to detect a condition indicative of the presence of a magnetic resonance imaging (MRI) device, switch operation of the IMD from a first pacing therapy program to a second pacing therapy program in response to detecting the condition indicative of the presence of the MRI device, and while operating in the second pacing therapy program, deliver a pacing pulse to an atrium of a heart of a patient during a time period between the end of an atrial refractory period of a previous atrial depolarization and the end of a ventricular refractory period of a previous ventricular depolarization corresponding to the previous atrial depolarization.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
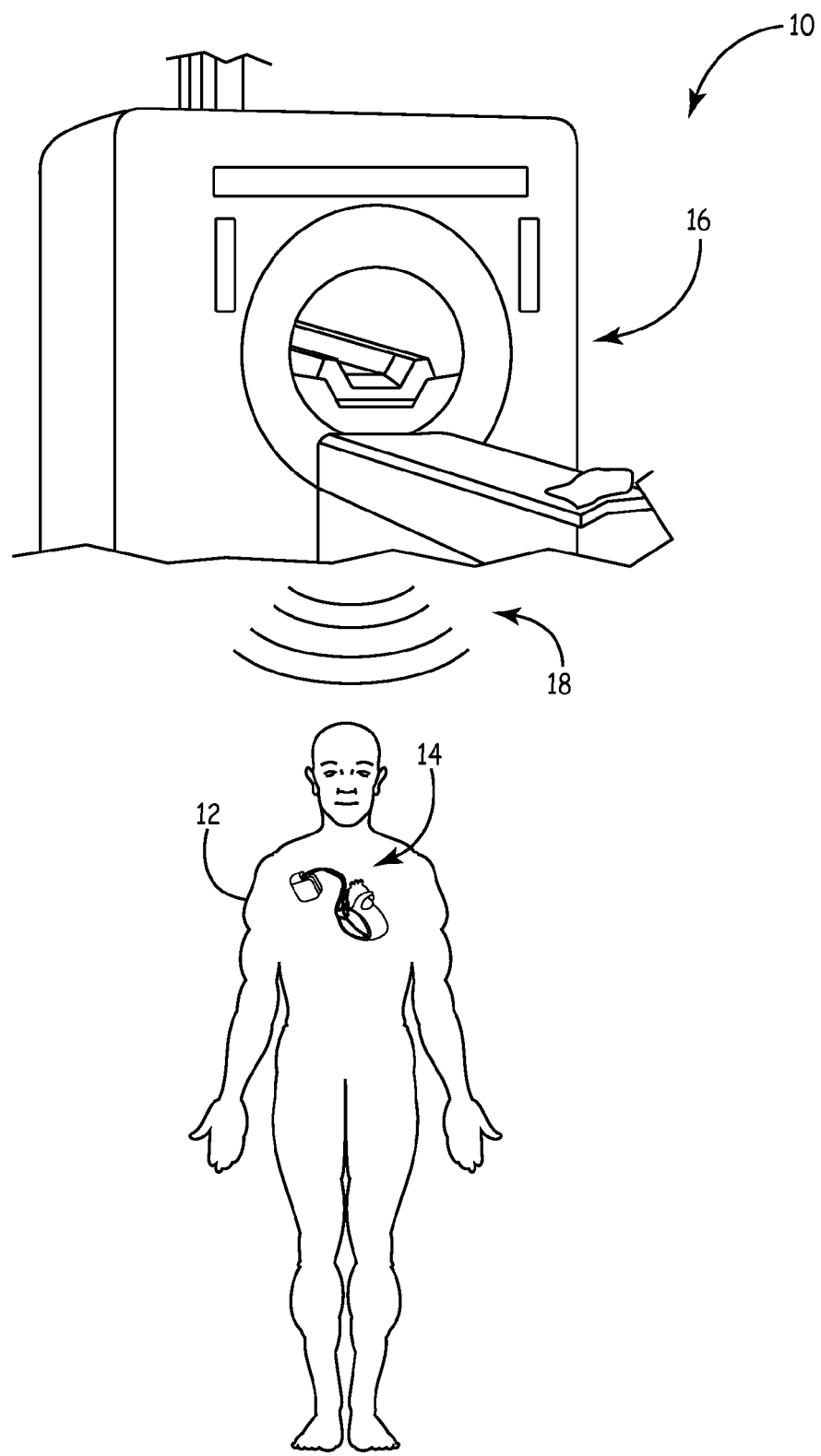
FIG. 1 is a conceptual diagram illustrating a magnetic resonance imaging (MRI) environment that includes an MRI device.

FIG. 1 is a conceptual diagram illustrating a magnetic resonance imaging (MRI) environment 10 that includes an MRI device 16. MRI device 16 may include a patient table on which patient 12 is placed prior to and during an MRI scan. The patient table is adjusted to position at least a portion of patient 12 within a bore of MRI device 16 (the "MRI bore"). While positioned within the MRI bore, patient 12 is subjected to a number of magnetic and RF fields to produce images of the portion of the body within the bore for diagnosing injuries, diseases, and/or disorders.

MRI device 16 includes a scanning portion that houses a primary magnet of MRI device 16 that generates a static MRI field. The static MRI field is a large non time-varying magnetic field that is typically always present around MRI device 16 whether or not an MRI scan is in progress. MRI device 16 also includes a plurality of gradient magnetic field coils that generate gradient magnetic fields. Gradient magnetic fields are pulsed magnetic fields that are typically only present while the MRI scan is in progress. MRI device 16 further includes one or more RF coils that generate RF fields. RF fields are pulsed high frequency fields that are also typically only present while the MRI scan is in progress.

The magnitude, frequency or other characteristic of the static MRI field, gradient magnetic fields and RF fields may vary based on the type of MRI device 16 producing the field or the type of MRI procedure being performed. A 1.5 T MRI device, for example, will produce a static magnetic field of approximately 1.5 Tesla and have a corresponding RF frequency of approximately 64 megahertz (MHz) while a 3.0 T MRI device will produce a static magnetic field of approximately 3.0 Tesla and have a corresponding RF frequency of approximately 128 MHz. However, other MRI devices may generate fields of different magnitude or frequency.

Figure 2:
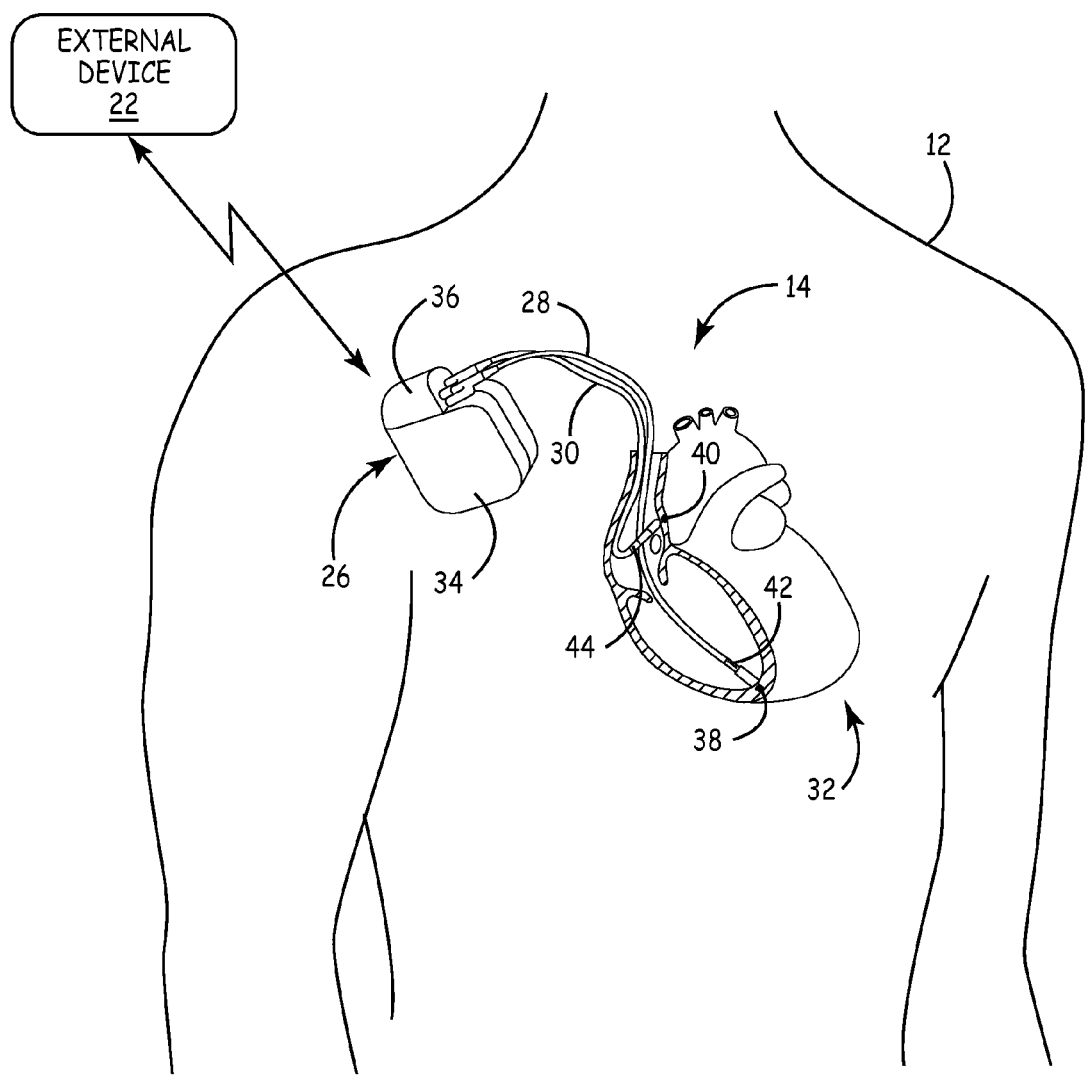
FIG. 2 is a conceptual diagram of an example implantable medical system that provides electrical stimulation therapy to a heart of a patient.

Patient 12 is implanted with an implantable medical system 14. Implantable medical system 14 may include an IMD connected to one or more leads. FIG. 2 is a conceptual diagram of an example implantable medical system 14 that provides electrical stimulation therapy to a heart 32 of patient 12. Heart 32 includes four chambers, namely the right atrium (RA), left atrium (LA), right ventricle (RV), and left ventricle (LV). A cardiac cycle commences with the generation of a depolarization impulse within the right atrium. In a normally functioning heart, the depolarization impulse is generated intrinsically. In a heart with electrical abnormalities, the depolarization may be generated by delivery of a pacing pulse to the atrium. The impulse then conducts through the right atrium to the left atrium and, after a short delay (e.g., approximately 50 milliseconds), the atria contract to push blood into the ventricles. The depolarization impulse continues to conduct down the heart to the right and left ventricles to cause the ventricles to contract pushing blood to the lungs and the rest of the body, respectively. In a heart with electrical abnormalities, the impulse in the atria may not conduct to the ventricles. In this case, the depolarization in the ventricles may also be generated by delivery of a pacing pulse to the ventricle(s).

After the contractions of the chambers, the respective chambers of the heart repolarize, during which the chambers of heart 32 are refractory. During the refractory period the chambers will either not depolarize in response to an electrical impulse (sometimes referred to as absolute refractory) or will only depolarize in response to a strong stimulus and/or the depolarization may be depressed (sometimes referred to as relative refractory period).

Implantable medical system 14 includes an IMD 26 connected to leads 28 and 30 to deliver electrical stimulation (e.g., pacing pulses) to one or more chambers of heart 32. In the example illustrated in FIG. 2, lead 28 is implanted within a right ventricle of heart 32 and lead 30 is implanted within a right atrium of heart 32. In one example, IMD 26 may be an implantable pacemaker that provides cardiac pacing to heart 32. In other examples, IMD 26 may be an implantable cardiac device that provides other electrical stimulation therapy in addition to pacing therapy, such as an implantable cardioverter defibrillator (ICD) or a cardiac resynchronization therapy defibrillator (CRT-D).

IMD 26 includes a housing 34 and a connector block 36. Housing 34 and connector block 36 may form a hermetic seal that protects components of IMD 26. In some examples, housing 34 may comprise a metal or other biocompatible enclosure having separate halves. Connecter block 36 may include electrical feedthroughs, through which electrical connections are made between conductors within leads 28 and 30 and electronic components included within housing 34. As will be described in further detail herein, housing 34 may house one or more processors, memories, transmitters, receivers, sensors, sensing circuitry, therapy circuitry and other appropriate components. Housing 34 is configured to be implanted in a patient, such as patient 12.

Leads 28 and 30 each include one or more electrodes. In the example illustrated in FIG. 2, leads 28 and 30 each include tip electrodes 38 and 40 and ring electrodes 42 and 44 located near a distal end of their respective leads 28 and 30. When implanted, tip electrodes 38 and 40 and/or ring electrodes 42 and 44 are placed relative to or in a selected tissue, muscle, nerve or other location within the patient 12. Although leads 28 and 30 are illustrated as including respective tip and ring electrodes, in other examples, one or both of leads 28 or 30 (or other lead) may include one or more than two electrodes. For example, a quadripolar lead may be provided that includes four electrodes (e.g., a hemispherical tip electrode and three ring electrodes or four ring-type electrodes) for use in multi-pole pacing applications.

In the example illustrated in FIG. 2, tip electrodes 38 and 40 are extendable helically shaped electrodes to facilitate fixation of the distal end of leads 28 and 30 to the target location within patient 12. In this manner, tip electrodes 38 and 40 are formed to define a fixation mechanism. In other embodiments, one or both of tip electrodes 38 and 40 may be formed to define fixation mechanisms of other structures. In other instances, leads 28 and 30 may include a fixation mechanism separate from tip electrode 38 and 40. For example, tip electrode 38 may take a different shape, such as a hemispherical electrode, and fixation mechanisms can be any appropriate type, including a grapple mechanism, a helical or screw mechanism, a drug-coated connection mechanism in which the drug(s) serves to reduce infection and/or swelling of the tissue, or other attachment mechanism.

One or more conductors (not shown in FIG. 2) extend within leads 28 and 30 from connector block 36 along the length of the lead to engage respective tip electrodes 38 and 40 and ring electrode 42 and 44. In this manner, each of electrodes 38, 40, 42 and 44 is electrically coupled to at least one respective conductor within its associated lead body. For example, a first electrical conductor can extend along the length of the body of lead 28 from connector block 36 and electrically couple to tip electrode 38 and a second electrical conductor can extend along the length of the body of lead 28 from connector block 36 and electrically couple to ring electrode 42. The respective conductors may electrically couple to circuitry, such as a therapy module or a sensing module, of IMD 26 via connections in connector block 36. The electrical conductors transmit therapy from the therapy module within IMD 26 to one or more of electrodes 38, 40, 42, and 44 and transmit sensed electrical signals from one or more of electrodes 38, 40, 42, and 44 to the sensing module within IMD 26.

In addition to providing cardiac pacing, IMD 26 may provide other electrical stimulation therapy, such as defibrillation, cardiac resynchronization, or cardioversion therapy. In this case, leads 28 and 30 may include additional electrodes. For example, one or both of leads 28 and 30 may include one or more elongated electrodes, which may, in some instances, take the form of a coil. IMD 26 may deliver defibrillation or cardioversion shocks to the heart via any combination of the elongated electrodes and housing electrode.

In addition to more or fewer electrodes on leads 28 or 30, implantable medical system 14 may include more or fewer leads extending from IMD 26. For example, IMD 26 may be coupled to a third lead implanted within a left ventricle of heart 32 of patient 12. In another example, IMD 22 may be coupled to a single lead that is implanted within an atrium of heart 32 of patient 12. As such, IMD 26 may be used for single chamber or multi-chamber cardiac rhythm management therapy. Additionally, leads 28 and/or 30 may not be implanted within heart 32 of patient 12, as is the case with epicardial leads. In other embodiments, IMD 26 may not be coupled to any leads, as is the case for a leadless pacemaker.

Some or all of the various types of fields produced by MRI device 16 may have undesirable effects on implantable medical system 14. In one example, the gradient magnetic fields and/or the RF fields generated during the MRI scan may induce energy on the conductors of leads 28 or 30 (e.g., in the form of a current). The induced energy on leads 28 or 30 may be conducted to IMD 26 and inappropriately detected as physiological signals, a phenomenon often referred to as oversensing. The detection of the induced energy on the leads 28 or 30 as physiological signals may result in IMD 26 delivering therapy when it is not desired (e.g., triggering a pacing pulse) or withholding therapy when it is desired (e.g., inhibiting a pacing pulse) when operating in the normal operating mode.

To reduce the adverse effects that may be caused by the fields of MRI device 16, IMD 26 is configured to operate in an MR conditional operating mode or MR conditional mode in accordance with the techniques of this disclosure. Operation of IMD 26 in the "MR conditional mode" may refer to an operating state of IMD 26 that it is less susceptible to being adversely affected by the gradient magnetic fields and RF fields emitted by MRI device 16 than the "normal mode" of operation. When operating in the MR conditional mode, IMD 26 is configured to operate with different functionality compared to the normal mode of operation.

Current clinical practice is to select a pacing therapy program for use during the MR conditional mode that provides asynchronous pacing for pacemaker-dependent patients at a rate above the intrinsic rate of patient 12 and to limit the duration of the asynchronous pacing. However, there is a possibility that the condition of patient 12 could change during the period of time their pacemaker is programmed to an asynchronous pacing mode. For example, some patients may experience an increase in their intrinsic heart rate during asynchronous pacing (e.g., due to increased anxiety when in the bore of an MRI scanner), which could result in competitive pacing. The pacing techniques of this disclosure provide a mechanism to reduce the likelihood of competitive pacing by decreasing the intrinsic heart rate during pacing therapy programs that provide pacing independent of underlying cardiac activity. In addition, pacing at a rate closer to the intrinsic heart rate of patient 12 could reduce the likelihood of symptoms that are sometimes induced by asynchronous pacing at higher rates.

In accordance with the techniques of this disclosure, the pacing therapy program utilized during the MR conditional mode provides an atrial pacing pulse after the atrial refractory period of a previous atrial depolarization expires, but prior to expiration of the ventricular refractory period of a ventricular depolarization corresponding to the previous atrial depolarization. The result of the atrial pacing pulse after the atrial refractory period of the previous atrial depolarization and before the expiration of the ventricular refractory period is two atrial depolarizations during a single cardiac cycle. Such a technique may be utilized when the pacing therapy program of the MR conditional mode is a synchronous pacing therapy program or a therapy pacing program that provides pacing independent of the underlying cardiac activity. IMD 26 may be configured to use other sensors (e.g., a pressure or acceleration sensor), different sense circuitry, or different sense algorithms to more accurately detect cardiac activity of patient 12 such that synchronous pacing may be provided while operating in the MR conditional mode.

In addition to adjustments to the pacing and sensing functionality, IMD 26 may also be configured to turn off high voltage therapy (e.g., defibrillation therapy) while operating in the MR conditional mode, to turn off telemetry functionality during operation in the MR conditional mode, and/or to make other adjustments. By configuring IMD 26 into the MR conditional mode, patient 12 having implanted medical system 14 may receive an MRI procedure with a reduced likelihood of interference with operation of IMD 26.

IMD 26 may transition to the MR conditional mode automatically, e.g., in response to detecting the presence of MRI device 16, or manually, e.g., in response from a command from an external programming device. After the MRI procedure is complete, IMD 26 transitions back to the normal mode of operation. IMD 26 may automatically revert to the normal mode of operation in response to no longer detecting the presence of MRI device 16, after expiration of a timer, or in response to some other predefined criteria, or a combination thereof. Alternatively, IMD 26 may be manually programmed into the normal mode of operation via a command received from the external programming device via wireless telemetry.

Implantable medical system 14 is also illustrated in FIG. 2 in conjunction with an external device 22, such as an external programmer IMD 26 may communicate with external device 22 using any of a variety of wireless communication techniques known in the art. Examples of communication techniques may include, for example, low frequency inductive telemetry or RF telemetry, although other techniques are also contemplated. Programmer 22 may be a handheld computing device, desktop computing device, a networked computing device, or other computing device configured to communicate with IMD 26. Programmer 22 may include a non-transitory computer-readable storage medium containing instructions that, when executed, cause a processor of external device 22 to provide the functions attributed to external device 22 in the present disclosure.

External device 22 retrieves data from IMD 26. Data retrieved from IMD 26 using external device 22 may include cardiac EGMs stored by IMD 26 that indicate electrical activity of heart 32. Data may also include marker channel data that indicates the occurrence and timing of sensing, diagnosis, and therapy events associated with IMD 26. Additionally, data may include information regarding the performance or integrity of IMD 26 or other components of implantable medical system 14, such as leads 28 and 30, or a power source of IMD 26. External device 22 may also transfer data to IMD 26. Data transferred to IMD 26 using external device 22 may include, for example, values for operational parameters, electrode selections used to deliver electrical stimulation, waveform selections used for electrical stimulation, configuration parameters for detection algorithms, or the other data. Although not illustrated in FIG. 2, IMD 26 may communicate with other devices not implanted within patient 12, such as a patient monitor.

Figure 3:
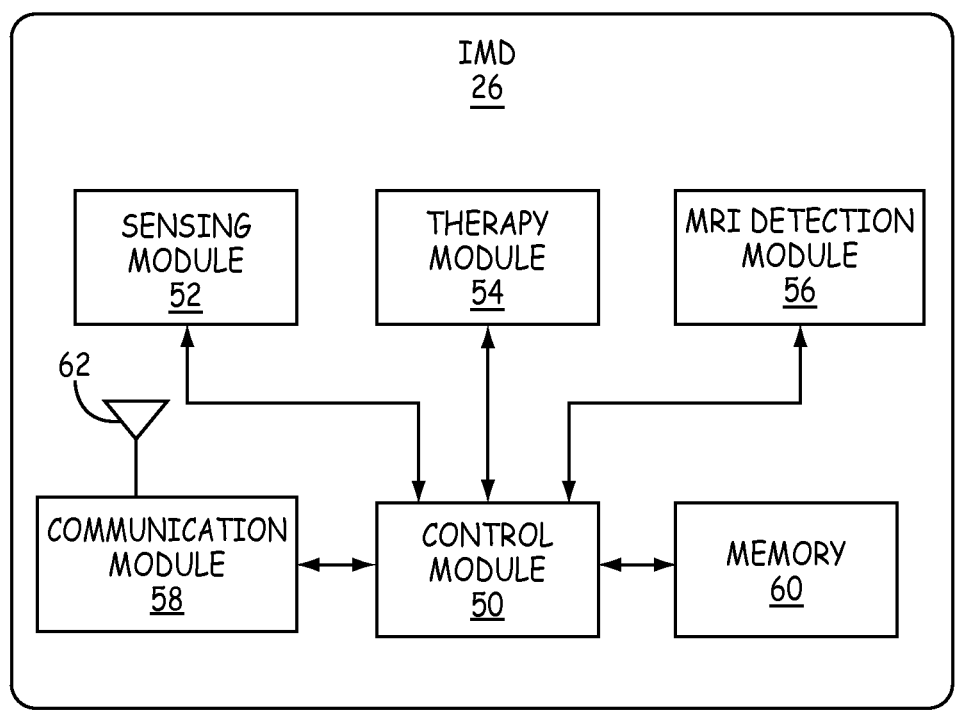
FIG. 3 is a functional block diagram of an example configuration of electronic components of an implantable medical device.

FIG. 3 is a functional block diagram of an example configuration of electronic components of IMD 26. IMD 26 includes a control module 50, sensing module 52, therapy module 54, MRI detection module 56, communication module 58, and memory 60. The electronic components may receive power from a power source (not shown in FIG. 3), which may be a rechargeable or non-rechargeable battery. In other embodiments, IMD 26 may include more or fewer electronic components. Additionally, any of the described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Therapy module 54 is configured to generate and deliver electrical stimulation therapy to heart 32. Therapy module 54 may include one or more pulse generators, capacitors, and/or other components capable of generating and/or storing energy to deliver as pacing pulses. Control module 50 may control therapy module 54 to generate electrical stimulation therapy and deliver the generated therapy to heart 32 via one or more combinations of electrodes 38, 40, 42, 44, and an indifferent housing electrode according to one or more therapy programs, which may be stored in memory 60. Control module 50 controls therapy module 54 to generate electrical pacing pulses with the amplitudes, pulse widths, timing, frequencies, electrode combinations or electrode configurations specified by a selected therapy program.

Therapy module 54 may deliver pacing pulses via a bipolar electrode configuration using pairs of tip and ring electrodes, such as tip and ring electrodes 38 and 42 of lead 28 or tip and ring electrodes 40 and 44 of lead 30. In other instances, therapy module 54 may deliver pacing pulses via a unipolar electrode configuration, e.g., using electrodes 38 and 40 in combination with a housing electrode of IMD 26. Therapy module 54 may include a switch module (not shown) that control module 50 may configure to select which of the available electrodes are used to deliver the stimulation therapy. Therapy module 54 may deliver one or more of these types of stimulation in the form of other signals besides pulses or shocks, such as sine waves, square waves, or other substantially continuous signals. In addition to pacing pulses, therapy module 54 may be configured to generate and deliver other forms of electrical stimulation therapy to heart 32, such as cardiac resynchronization pacing pulses, cardioversion pulses, or defibrillation pulses, under to the control of control module 50.

Sensing module 52 is electrically coupled to some or all of electrodes 38, 40, 42, and 44 via the conductors of leads 28 and 30, or to the housing electrode via conductors internal to housing 26. Sensing module 52 is configured to obtain signals sensed via one or more combinations of electrodes 38, 40, 42, and 44 and the housing electrode and process the obtained signals. The components of sensing module 52 may be analog components, digital components or a combination thereof. Sensing module 52 may, for example, include one or more sense amplifiers, filters, rectifiers, threshold detectors, analog-to-digital converters (ADCs) or the like. Sensing module 52 may convert the sensed signals to digital form and provide the digital signals to control module 50 for processing or analysis. For example, sensing module 52 may amplify signals from the sensing electrodes and convert the amplified signals to multi-bit digital signals by an ADC. Sensing module 52 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 50.

Control module 50 may process the signals from sensing module 52 to monitor electrical activity of heart 32 of patient 12. Control module 50 may store signals obtained by sensing module 52 as well as any generated EGM waveforms, marker channel data or other data derived based on the sensed signals in memory 60. Control module 50 may analyze the EGM waveforms and/or marker channel data to detect cardiac events (e.g., tachyarrhythmias). In further examples, sensing module 52 is coupled to one or more sensors that are not included on leads 28 or 30, e.g., via a wired or wireless coupling. Such sensors may include pressure sensors, accelerometers, flow sensors, blood chemistry sensors, activity sensors, magnetic field sensors or other types of physiological sensors. These additional sensors may be used in conjunction with or separately to monitor the electrical activity of heart 32 of patient 12 and/or other aspect of the general cardiac health of patient 12.

Control module 50 may, in some instances, control pacing therapy provided by therapy module 54 as a function of the sensed electrical signals. Control module 50 may utilize the sensed electrical signals obtained by sensing module 52 (or lack of sensed electrical signals) to trigger delivery of pacing pulses and/or inhibit delivery of pacing pulses. In other instances, control module 50 may control pacing therapy without regard to the sensed electrical signals on leads 28 and 30.

As described above, the RF and/or gradient magnetic fields produced by MRI device 16 may have undesirable effects on implantable medical system 14. As such, control module 50 is configured to operate IMD 26 in an MR conditional mode when exposed to MRI device 16 or other device or environment having fields that may have undesirable effects on operation of implantable medical system 14.

Control module 50 may automatically configure IMD 26 to operate the MR conditional mode in response to detecting a condition indicative of the presence of MRI device 16. MRI detection module 56 of IMD 26 may, for example, include one or more sensors or be coupled to one or more sensors that monitor for one or more particular characteristics associated with the presence of MRI device 16, e.g., one or more characteristics associated with the static or gradient magnetic fields and/or the RF fields generated by MRI device 16. Control module 50 may use information provided by MRI detection module 56 alone or in conjunction with other information to detect the condition indicative of the presence of MRI device 16. MRI detection module 56 may include any type of sensor that provides information indicative of the characteristics of the MRI device including, but not limited to one or more of a Hall effect sensor, a reed switch, a magnetic gradient sensor, an antenna, a radiofrequency (RF) sensing device, or other sensors or combination of sensors.

In one example, MRI detection module 56 may include a magnetic field sensor having an output that varies as a function of the magnitude of a magnetic field to which it is exposed and control module 50 may analyze the output of the magnetic field sensor and detect presence of MRI device 16. In this case, control module 50 may detect the presence of MRI device 16 when the magnitude of the magnetic field exceeds a threshold field strength, e.g., the magnetic field exceeds 1.0 Tesla. In another example, the MRI detection module 56 may analyze more than one parameter, such as the strength of the magnetic field and a frequency of an RF field or the directionality of the magnetic field. In this case, control module 50 may detect the presence of MRI device 16 when any magnetic field is detected in conjunction with the presence of RF fields having frequencies of 64 or 128 MHz. In other instances, control module 50 may make the determination based on other information from MRI detection module 56 in addition to or instead of the magnetic field strength.

In some embodiments, IMD 26 may not include an MRI detection module 56. Instead, control module 50 may obtain, via antenna 62 and communication module 58, a communication from an external device (e.g., external device 22 of FIG. 2 or MRI device 16 of FIG. 1) indicating that IMD 26 is being exposed to or will soon be exposed to MRI device 16. For example, control module 50 may receive a command to switch to the MR conditional operating mode. In this case, the communication or command from external device 22 may be considered the condition indicative of the presence of MRI device 16.

Communication module 58 includes any suitable hardware, firmware, software or any combination thereof for communicating with another device, such as external device 22 or MRI device 16, by wireless telemetry. For example, communication module 58 may include appropriate modulation, demodulation, frequency conversion, filtering, and amplifier components for transmission and reception of data with the aid of antenna 62. Antenna 62 may be located within connector block 36 of IMD 26 or within housing 34 of IMD 26. In one example, antenna 62 may be an inductive coil antenna within housing 34 of IMD 26. In another example, antenna 62 may be an RF antenna located within connector block 36 and coupled to communication module 58 via a feedthrough. In a further example, IMD 26 may include both an inductive coil antenna and an RF antenna coupled to communication module 58 or other antenna located within or outside of housing 34.

In response to the output of MRI detection module 56 indicating presence of MRI device 16 or in response to a communication received from a programmer to configure the MR conditional operating mode, control module 50 transitions operation of IMD 26 from a current operating mode (e.g., a normal operating mode) to the MR conditional mode. The MR conditional mode may include a pacing therapy program that provides pacing therapy independent of underlying cardiac activity or a synchronous pacing therapy program (e.g., in instances in which sensing module 52 is capable of reliable sensing during exposure to fields of MRI device 16) that provides pacing therapy based on the underlying cardiac activity.

Regardless of whether the MR conditional mode provides pacing therapy as a function of the underlying cardiac activity, control module 50 is configured to control therapy module 54 to generate and deliver an atrial pacing pulse (e.g., via one or more of electrodes 40 or 44 of lead 30 and/or the indifferent housing electrode) after expiration of the atrial refractory period associated with a previous atrial depolarization, but before expiration of the ventricular refractory period associated with the ventricular depolarization associated with the previous atrial depolarization.

Control module 50 controls therapy module 54 to provide the atrial pacing pulse via one or both of electrodes 40 and 44 and/or the housing electrode during a defined time window. The defined time window extends from the point at which the atrial tissue to be stimulated becomes non-refractory up to the point at which the stimulated atrial depolarization could propagate to the ventricles to cause a ventricular depolarization. In other words, the time period extends from the end of the atrial refractory period of the previous atrial depolarization to the end of the ventricular refractory period of the corresponding ventricular depolarization.

Refractory period timing and durations may vary with the individual and with the underlying heart rhythm, and thus the duration of the time window will also vary. Therefore, the time window may be defined based upon a preceding atrial depolarization, ventricular depolarization, or possibly both. The time window may, in one example, be between about 80 milliseconds (ms) to about 200 ms following a normally conducted ventricular depolarization. A normally conducted ventricular depolarization in this example is a ventricular depolarization preceded by an atrial depolarization at an interval corresponding to a relatively normal A-V conduction interval (e.g., not a premature ventricular depolarization (PVC)). Timing of the stimulus pulses may be predefined by the attending physician and programmed into the device or may be varied by the device.

As described above, IMD 26 may not be able to reliably sense during an MRI procedure and thus the MR conditional mode may include a pacing therapy program that delivers pacing therapy independent of underlying cardiac activity. In some instances, such as in cases in which patient 12 has sick sinus syndrome or normal atrioventricular conduction, the pacing therapy program may provide pacing to the atrium only. Because IMD 26 is not able to reliably sense, delivery of the atrial pacing pulse during the defined time window (e.g., between the end of the atrial refractory period and the end of the ventricular refractory period) may be triggered at a defined interval following delivery of the preceding atrial pacing pulse. For example, control module 50 may control therapy module 54 to generate and deliver the additional atrial pacing pulse between approximately 120 ms to about 320 ms following the delivery of the preceding atrial pacing pulse and, more preferably between approximately 120 ms to about 320 ms following the delivery of the preceding atrial pacing pulse.

In other instances, the pacing therapy program may provide pacing to both the atrium and the ventricle independent of underlying cardiac activity. In this case, the delivery of the additional atrial pacing pulse may be triggered at a defined interval following delivery of the preceding atrial pacing pulse (as described in the previous paragraph) or a defined interval following delivery of the ventricular pacing pulse. For example, control module 50 may control therapy module 54 to deliver the additional atrial pacing pulse between 80 ms to about 200 ms following the delivery of the preceding ventricular pacing pulse.

IMD 26 may, in other instances, be capable of reliably sensing during the MRI procedure, e.g., using alternative sensing techniques or signal processing techniques. Even though sensing is possible, control module 50 may still control therapy module 54 to provide a pacing therapy program that provides pacing independent of underlying cardiac activity while operating in the MR conditional mode. However, the time window for providing the additional atrial pacing pulse may be determined based upon the occurrence of an atrial depolarization (sensed or paced) or a normally conducted ventricular depolarization (e.g., sensed or paced).

In further instances, control module 50 may control therapy module 54 to provide a synchronous pacing therapy program when capable of reliably sensing during the MRI procedure. Even if a synchronous pacing therapy program is provided during the MR condition mode, control module 50 may control therapy module 54 to generate and deliver an atrial pacing pulse during a defined time window, e.g., after expiration of the atrial refractory period, but prior to expiration of the ventricular refractory period.

The pacing techniques of this disclosure provide a mechanism to reduce the likelihood of competitive pacing during the MR conditional mode by decreasing the intrinsic heart rate instead of providing asynchronous pacing at a rate greater than the intrinsic heart rate of patient 12. In addition, by reducing the rate of pacing to a rate closer to the intrinsic heart rate of patient 12, the likelihood of symptoms that are sometimes induced by asynchronous pacing at higher rates may be reduced.

Control module 50 may suspend operation of other functionality of IMD 26 while operating in the MR conditional mode. For example, control module 50 may suspend tachycardia detection and therapy, fibrillation detection and therapy, impedance measurements, battery measurements, or the like. Control module 50 may perform some of the functions in a different manner. For example, control module 50 may use a different sensor or algorithm to detect cardiac activity of the heart of patient 12, such as pressure sensor measurements rather than electrical activity of the heart.

The various modules of IMD 26 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 60 may include computer-readable instructions that, when executed by control module 50 or other component of IMD 26, cause one or more components of IMD 26 to perform various functions attributed to those components in this disclosure. Memory 60 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 4A:
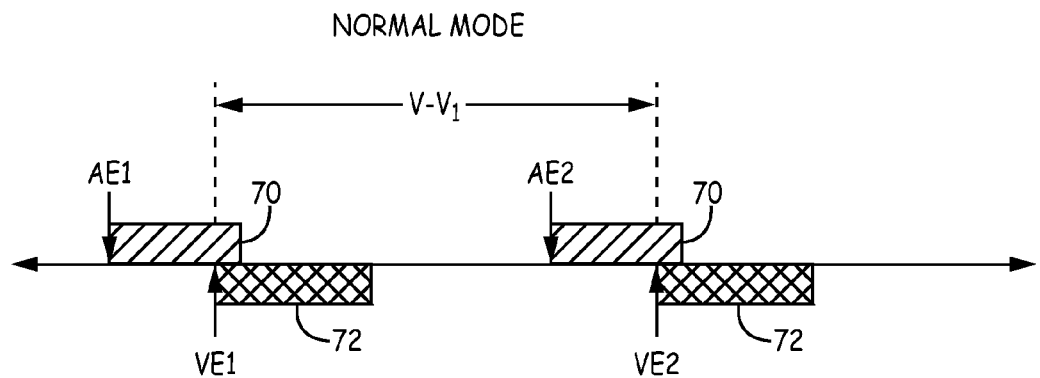
FIGS. 4A and 4B are marker channel diagrams illustrating example pacing therapy programs utilized during the normal mode and the MR conditional mode, respectively.
Figure 4B:
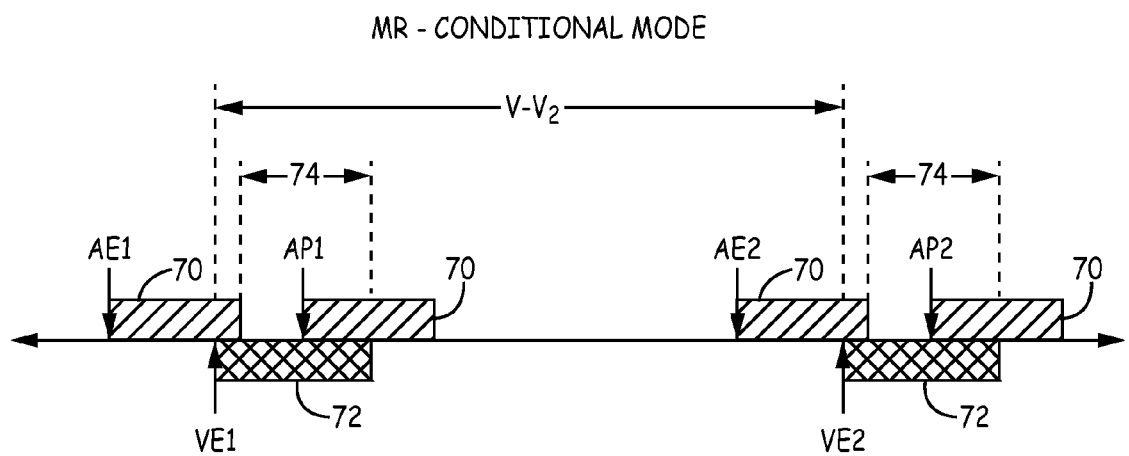

FIGS. 4A and 4B are marker channel diagrams illustrating example pacing therapy programs utilized during the normal mode and the MR conditional mode, respectively. During the normal mode, IMD 26 is configured with a conventional pacing therapy program in which there is generally a one-to-one correspondence between atrial events and ventricular events during each cardiac cycle. As illustrated in FIG. 4A, a first cardiac cycle includes a first atrial event AE1 occurs followed by a corresponding first ventricular event VE1. The first atrial event AE1 may be a sensed atrial event corresponding to an intrinsic (or spontaneous) atrial depolarization or it may be a paced atrial event corresponding to delivery of a pacing pulse by IMD 26. Likewise, the first ventricular event VE1 may be a sensed ventricular event corresponding to an intrinsic (or spontaneous) ventricular depolarization or it may be a paced ventricular event corresponding to delivery of a pacing pulse by IMD 26.

Following the depolarization (intrinsic or paced) of the atrium, the atrium is refractory for a period of time 70 (referred to herein as an atrial refractory period 70). Likewise, the ventricle is also refractory for a period of time 72 (referred to herein as a ventricular refractory period 72) following the depolarization (intrinsic or paced) of the ventricle. As mentioned above, during the refractory periods 70 and 72 the respective chambers of heart 32 will either not depolarize in response to an electrical impulse or will only depolarize in response to a strong stimulus and/or the depolarization may be depressed. Atrial refractory period 70 and ventricular refractory period 72 may be between approximately 150-250 ms.

Some period of time after the first atrial and ventricular events, a second cardiac cycle is initiated that includes a second atrial event AE2 followed by a corresponding second ventricular event VE2. Again, the second atrial and ventricular events may be sensed events, paced events, or a combination thereof. For a patient 12 having a heart rate (intrinsic or paced) of approximately 60 beats per minute (bpm), for example, the second cardiac cycle occurs approximately 1 second after the beginning of the first cardiac cycle. In other words, the second atrial event AE2 occurs approximately 1 second after the first atrial event AE1. Likewise, the second ventricular event VE2 occurs approximately 1 second after the first ventricular event VE1 (illustrated in FIG. 4A as V-V$_1$). IMD 26 may maintain an atrial pacing timer to determine when to initiate a subsequent cardiac cycle. The atrial pacing timer may, for example, be reset upon delivery or detection of atrial event AE1. IMD 26 may deliver a second pacing pulse to the atrium of the heart to initiate the second cardiac cycle upon expiration of the atrial pacing timer.

In accordance with the techniques of this disclosure, the MR conditional mode of IMD 26 is configured with a pacing therapy program in which there is not a one-to-one correspondence between atrial events and ventricular events in a single cardiac cycle. As illustrated in FIG. 4B, a first cardiac cycle again includes a first atrial event AE1 followed by a corresponding first ventricular event VE1. The first atrial event AE1 may be a sensed atrial event corresponding to an intrinsic (or spontaneous) atrial depolarization or it may be a paced atrial event corresponding to delivery of a pacing pulse by IMD 26. Likewise, the first ventricular event VE1 may be a sensed ventricular event corresponding to an intrinsic (or spontaneous) ventricular depolarization or it may be a paced ventricular event corresponding to delivery of a pacing pulse by IMD 26.

Following each depolarization, the respective chamber of the heart is refractory. This again is represented by refractory periods 70 and 72. Following the first ventricular event VE1, IMD 26 delivers an atrial pacing pulse AP1 during time window 74 during the first cardiac cycle. Time window 74 extends from the end of the atrial refractory period 70 through the end of the ventricular refractory period 72. In other words, the time window 74 extends from the point at which the atrial tissue becomes non-refractory up to the point at which the ventricular tissue becomes non-refractory. In one example, time window 74 may extend within a time period occurring between about 80-200 ms following ventricular depolarization VE1.

IMD 26 may maintain a refractory pacing timer to determine the time at which to deliver the atrial pacing pulse AP1. The refractory pacing timer may be defined based upon the preceding atrial event AE1, the preceding ventricular event VE1, or a combination thereof. In the example of FIG. 4B, IMD 26 delivers AP1 toward the middle of time period 74. However, IMD 26 may deliver the atrial pacing pulse AP1 anywhere within time period 74. For example, IMD 26 may deliver the atrial pacing pulse AP1 toward the beginning of time period 74 just after the atrium becomes non-refractory or toward the end of time period 74 just before the ventricle becomes non-refractory.

By delivering atrial pacing pulse AP1 during time window 74, the atrium of heart 12 captures and depolarizes, but the impulse is not conducted to the ventricle because the ventricle is still refractory. As such, a new atrial refractory period 70 begins in the atrium. Some period of time after the atrial pacing pulse AP1, a second cardiac cycle is initiated with a second atrial event AE2 followed by a corresponding second ventricular event VE2. Again the second atrial and ventricular events may be sensed events, paced events, or a combination thereof. Following the second ventricular event VE2, IMD 26 delivers an atrial pacing pulse AP2 within the second cardiac cycle during time window 74.

Control module 50 may be configured to determine the timing of a subsequent atrial pacing pulse associated with a next cardiac cycle based on the delivery of the pacing pulse to the atrium of the heart of the patient during the time period between the end of the atrial refractory period of the previous atrial depolarization and the end of the ventricular refractory period of the previous ventricular depolarization corresponding to the previous atrial depolarization. As described above, IMD 26 may maintain an atrial pacing timer to determine when to initiate a subsequent cardiac cycle. In the example of FIG. 4B, the atrial pacing timer may be reset upon delivery of atrial pacing pulse AP1. IMD 26 may deliver a pacing pulse to the atrium of the heart to initiate the second cardiac cycle upon expiration of the atrial pacing timer, e.g., at AE2 in the example of FIG. 4B.

For a patient having a heart rate (intrinsic or paced) of approximately 60 bpm, AE2 would occur approximately 1 second after the previous atrial event. In this case, the atrial pacing pulse AP1 causes the atrium to again depolarize and repolarize, and AE2 would occur approximately 1 second after atrial pacing pulse AP1 instead of approximately 1 second after atrial event AE1. In effect the atrial pacing pulse AP1 resets the timing of the atrium without causing the ventricle to depolarize a second time in response to atrial pacing pulse AP1. The effect is that the V-V interval (V-$V_2$) is extended by the amount of time between atrial event AE1 and subsequent atrial pacing pulse AP1, thus slowing the heart rate of patient 12. The refractory pacing timer used to determine the time at which to deliver the atrial pacing pulse AP1 may be set to achieve a desired heart rate.

Figure 5:
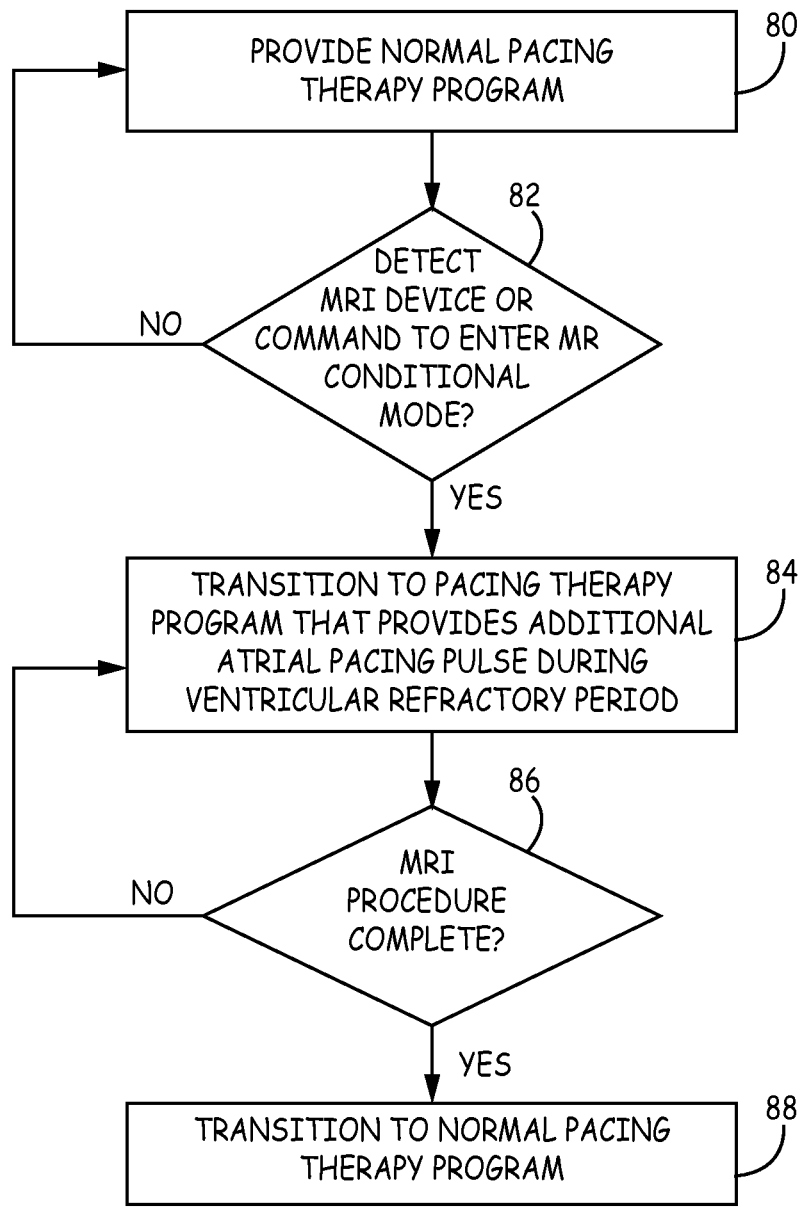
FIG. 5 is a flow diagram illustrating example operation of an implantable medical device operating in accordance with the techniques of this disclosure.

FIG. 5 is a flow diagram illustrating example operation of IMD 26 operating in accordance with the techniques of this disclosure. IMD 26 is initially configured in a normal operating mode that provides a conventional pacing therapy program (block 80). The conventional pacing therapy program may, in one example, be a synchronous pacing mode in which pacing pulses are provided based on sensed cardiac data, e.g., pacing pulses are triggered and/or inhibited based on the sensed cardiac data. As described above, detection of the MRI-induced energy on the leads 28 or 30 as physiological signals may result in IMD 26 delivering pacing therapy when it is not desired (e.g., triggering a pacing pulse) or withholding therapy when it is desired (e.g., inhibiting a pacing pulse) when operating in accordance with a synchronous pacing therapy program.

IMD 26 determines whether MRI detection module 56 detects MRI device or communication module 58 receives a command to enter an MR conditional operating mode (block 82). When neither condition is detected ("NO" branch of block 82), IMD 26 continues to operate in the normal operating mode using the conventional pacing therapy program. When either condition is detected ("YES" branch of block 82), IMD 26 transitions to the MR conditional operating mode during which therapy module 54 is configured to provide an atrial pacing pulse after expiration of the atrial refractory period of a previous atrial depolarization of the cardiac cycle, but prior to expiration of the ventricular refractory period of a corresponding ventricular depolarization of the cardiac cycle (block 84). The MR conditional mode may also have additional adjustments to pacing and sensing functionality, e.g., high voltage therapy turned off, telemetry turned off, or the like.

IMD 26 determines whether the MRI procedure is complete (block 86). IMD 26 may automatically determine that the MRI procedure is complete in response to no longer detecting the presence of MRI device 16, after expiration of a timer, or in response to some other predefined criteria, or a combination thereof. Alternatively, IMD 26 may determine that the MRI procedure is complete upon receiving a command from the external programming device via wireless telemetry. When the MRI procedure is not complete ("NO" branch of block 86), IMD 26 continues to operate in accordance with the pacing program that provides an atrial pacing pulse after a normal ventricular contraction during a period of time after the atrial refractory period, but during the ventricular refractory period. When the MRI procedure is not complete ("YES" branch of block 86), IMD 26 transitions back to the normal pacing therapy program (block 88).

Although the techniques of this disclosure are described with respect to an environment in which IMD 26 is exposed to MRI device 16, the techniques may be used to control operation of IMD 26 within environments in which other types of interfering signals are present. For example, IMD 26 may operate in accordance with the techniques of this disclosure in environments in which a potentially interfering signal(s) is generated by other sources, such as electrocautery devices, diathermy devices, ablation devices, radiation therapy devices, electrical therapy devices, magnetic therapy devices, radio frequency identification (RFID) readers, or any other environment with devices that radiate energy to produce magnetic, electromagnetic, electric or other disruptive energy fields.

The techniques described in this disclosure, including those attributed to IMD 26, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a non-transitory computer-readable medium such as RAM, ROM, NVRAM, EEPROM, or flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
a therapy module configured to generate pacing therapy for a heart of a patient; and
a control module configured to detect a condition indicative of the presence of a magnetic resonance imaging (MRI) device, switch operation from a first pacing therapy program to a second pacing therapy program in response to detecting the condition indicative of the presence of the MRI device, and while operating in the second pacing therapy program, control the therapy module to generate a pacing pulse to an atrium of the heart of the patient during a time period between the end of an atrial refractory period of a previous atrial depolarization and the end of a ventricular refractory period of a previous ventricular depolarization corresponding to the previous atrial depolarization.

2. The implantable medical device of claim 1, further comprising a refractory pacing timer, wherein the control module is configured to control the therapy module to generate the pacing pulse to the atrium of the heart of the patient during the time period between the end of the atrial refractory period of the previous atrial depolarization and the end of the ventricular refractory period of the previous ventricular depolarization corresponding to the atrial depolarization upon expiration of the refractory pacing timer.

3. The implantable medical device of claim 2, wherein the refractory pacing timer is initiated in response to one of sensing the previous atrial depolarization and delivering a pacing pulse to the atrium to cause the previous atrial depolarization.

4. The implantable medical device of claim 2, wherein the refractory pacing timer is initiated in response to one of sensing the previous ventricular depolarization and delivering a pacing pulse to a ventricle to cause the previous ventricular depolarization.

5. The implantable medical device of claim 1, wherein the control module is configured to control the therapy module to generate pacing pulses independent of underlying cardiac activity.

6. The implantable medical device of claim 5, further comprising a sensing module configured to sense cardiac electrical signals from at least one chamber of the heart, wherein the control module is configured to control the therapy module to generate pacing therapy as a function of the sensed cardiac electrical signals in the first pacing therapy program.

7. The implantable medical device of claim 1, wherein the control module is configured to determine the timing of a next atrial pacing pulse associated with a next cardiac cycle based on the delivery of the pacing pulse to the atrium of the heart of the patient during the time period between the end of the atrial refractory period of the previous atrial depolarization and the end of the ventricular refractory period of the previous ventricular depolarization corresponding to the previous atrial depolarization.

8. The implantable medical device of claim 1, further comprising one or more sensors configured to generate an output as a function of one or more fields generated by the MRI device, wherein the control module is configured to detect the condition indicative of the presence of the MRI device based on the output of the one or more sensors.

9. The implantable medical device of claim 1, further comprising a communication module configured to receive communications from an external device, wherein the control module is configured to detect the condition indicative of the presence of the MRI device upon receiving a command via wireless telemetry to operate in accordance with the second pacing therapy program.

10. The system of claim 1, wherein the control module is configured to suspend at least one of tachycardia detection, tachycardia therapy, fibrillation detection, fibrillation therapy, impedance measurements, or battery measurements in response to detecting the condition indicative of the presence of the MRI device.

11. A method comprising:
operating an implantable medical device (IMD) in a first pacing therapy program;
detecting a condition indicative of the presence of a magnetic resonance imaging (MRI) device;

switching operation of the IMD from the first pacing therapy program to a second pacing therapy program in response to detecting the condition indicative of the presence of the MRI device; and while operating in the second pacing therapy program, delivering a pacing pulse to an atrium of a heart of a patient during a time period between the end of an atrial refractory period of a previous atrial depolarization and the end of a ventricular refractory period of a previous ventricular depolarization corresponding to the previous atrial depolarization.

12. The method of claim 11, further comprising:

maintaining a refractory pacing timer, wherein delivering the pacing pulse to the atrium of the heart of the patient during the time period between the end of an atrial refractory period of a previous atrial depolarization and the end of the ventricular refractory period of the previous ventricular depolarization corresponding to the atrial depolarization comprises delivering the pacing pulse upon expiration of the refractory pacing timer.

13. The method of claim 12, further comprising initiating the refractory pacing timer in response to one of sensing the previous atrial depolarization and delivering a pacing pulse to the atrium to cause the previous atrial depolarization.

14. The method of claim 12, further comprising initiating the refractory pacing timer in response to one of sensing the previous ventricular depolarization and delivering a pacing pulse to a ventricle to cause the previous ventricular depolarization.

15. The method of claim 11, wherein operating in the second pacing therapy program comprises delivering pacing pulses independent of underlying cardiac activity.

16. The method of claim 15, further comprising sensing cardiac electrical signals from at least one chamber of the heart, wherein operating in the first pacing therapy program comprises delivering pacing pulses as a function of sensed cardiac electrical signals.

17. The method of claim 11, further comprising determining the timing of a next atrial pacing pulse based on the delivery of the pacing pulse to an atrium of a heart of a patient during a time period between the end of an atrial refractory period of a previous atrial depolarization and the end of a ventricular refractory period of a previous ventricular depolarization corresponding to the previous atrial depolarization.

18. The method of claim 11, wherein detecting a condition indicative of the presence of the MRI device comprises one of detecting one or more fields associated with the MRI device and receiving a command via wireless telemetry that instructs the IMD to switch into the second pacing therapy program.

19. The method of claim 11, further comprising suspending at least one of tachycardia detection, tachycardia therapy, fibrillation detection, fibrillation therapy, impedance measurements, or battery measurements in response to detecting the condition indicative of the presence of the MRI device.

20. A computer-readable storage medium comprising instructions that, when executed, cause an implantable medical device (IMD) to:

detect a condition indicative of the presence of a magnetic resonance imaging (MRI) device;

switch operation of the IMD from a first pacing therapy program to a second pacing therapy program in response to detecting the condition indicative of the presence of the MRI device; and while operating in the second pacing therapy program, deliver a pacing pulse to an atrium of a heart of a patient during a time period between the end of an atrial refractory period of a previous atrial depolarization and the end of a ventricular refractory period of a previous ventricular depolarization corresponding to the previous atrial depolarization.

* * * * *